United States Patent [19]

Meister

[11] 4,274,279
[45] Jun. 23, 1981

[54] VISCOSITY MEASURING DEVICE

[75] Inventor: John J. Meister, Gainesville, Fla.

[73] Assignee: Phillips Petroleum Company, Bartlesville, Okla.

[21] Appl. No.: 964,400

[22] Filed: Nov. 28, 1978

[51] Int. Cl.$^3$ ............................................ G01N 11/06
[52] U.S. Cl. ......................................................... 73/55
[58] Field of Search ............... 73/55, 56, 64; 366/130; 368/93, 95; D10/44

[56] References Cited

U.S. PATENT DOCUMENTS

| | | | |
|---|---|---|---|
| 1,635,281 | 7/1927 | Larson | 73/56 |
| 1,659,534 | 2/1928 | Mason | 73/56 |
| 1,758,677 | 5/1930 | Smith | 73/56 |
| 1,869,718 | 8/1932 | Smith | 73/56 |
| 1,919,921 | 7/1933 | Anderson et al. | 73/55 |
| 2,048,305 | 7/1936 | Ubbelohde | 73/55 |
| 2,419,658 | 4/1947 | Rogers | 73/55 X |
| 3,659,825 | 5/1972 | Reiter | 366/130 |

OTHER PUBLICATIONS

Saita, T., *Closed-type Capillary Viscometer*, in Journal of Physics E., 9(12): pp. 1128-1130, Dec. 1976.
Kang et al., *Meas. Viscosity of Organic Electrolyte*, in Journal of Electrochemical Society, 122(9): pp. 1155-1160, Sep. 1975.
Fischer, M., *Ein Geschlossenes Kapillarviskosimeter*, in Glastechn. Ber. 46 Jahrgang Heftl., pp. 1-6, Jan. 1973.

*Primary Examiner*—Gerald Goldberg
*Assistant Examiner*—Joseph W. Roskos

[57] ABSTRACT

An improved measuring viscosity device comprises an upper container and a lower container, the upper container has a diameter greater than the lower container, the two containers are connected by a flow restricting conduit and also by an equalizing tube extending from a top portion of the lower container upwardly into the upper container through the bottom wall thereof so that no part of the equalizing tube extends outwardly from the axis of the device beyond the periphery of the upper container.

3 Claims, 5 Drawing Figures

VISCOSITY MEASURING DEVICE

This invention relates to the recovery of oil from a subterranean resevoir employing surfactant-cosurfactant systems. In one of its aspects it relates to the addition of such systems of a phase stabilizing agent. In a further aspect of the invention it relates to the use of such phase-stabilized systems for the recovery of oil from a subterranean formation.

In one of its concepts the invention provides a phase-stabilized composition comprising an aqueous saline solution of a petroleum sulfonate and at least one ethoxylated sulfosuccinate derivative, e.g., a diester and/or a half-ester of alpha-sulfosuccinic acid and an ethoxylated alcohol. In another of its concepts the invention provides a method for the recovery of oil from a subterranean formation using a phase-stabilized composition as herein described.

In post-primary oil recovery operations, the sulfosuccinate-petroleum sulfonate-cosurfactant mixture in a suitable brine can be injected into an oil-bearing subterranean formation to form a microemulsion in situ to improve tertiary oil recovery, also, the brine-sulfosuccinate-petroleum sulfonate-cosurfactant mixture can be equilibrated with formation oil to give a microemulsion and, then the microemulsion can be injected into the formation to improve tertiary oil recovery. The surfactant-containing slug can be optionally preceded by an aqueous preflush and then followed by thickened water and aqueous drive fluid. It is contemplated that the inventive surfactant systems can be advantageously used in connate water containing high concentrations of divalent ions such as $Ca^{++}$ and $Mg^{++}$.

It is an object of the present invention to provide a phase-stabilized surfactant-cosurfactant system useful in the production of oil from a subterranean formation. It is another object of the invention to provide a method for the improved recovery of oil from a subterranean formation.

Other aspects, concepts and objects are apparent from a study of this disclosure, the drawing and the appended claims.

According to the present invention an ethoxylated sulfosuccinate derivative, such as can be obtained by reaction of α-sulfosuccinic acid and an ethoxylated alcohol to produce a diester and/or a half-ester, is added as a phase stabilizing agent to a system comprising aqueous saline solution of petroleum sulfonate, a surfactant and a cosurfactant as such system is prepared for use to recover oil from a subterranean formation.

The diester sulfosuccinate derivatives in which the molar ratio of ethoxylated alcohol to α-sulfosuccinic acid is 2:1 can be described by the formula (A):

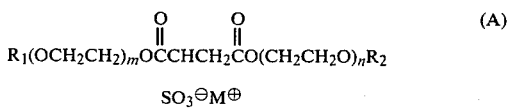

$$SO_3^\ominus M^\oplus$$

wherein $R_1$ and $R_2$ represent alkyl radicals, which can be different, containing three to eighteen carbon atoms. Generally, $R_1$ and $R_2$ will contain from five to sixteen carbon atoms each, preferred alkyl radicals containing from six to ten carbon atoms each. The cation M can be sodium, lithium, potassium, ammonium or substituted ammonium, and the sum of m+n can vary over the general range of 4 to 100, m or n being at least 1. Suitable substituted ammonium cations include anilinium, p-toluidinium, methylammonium, diethylammonium, isobutylammonium, trimethylammonium and the like. The cation M is preferably sodium at least because of price and availability.

The ethoxylated alcohols which are suitable for preparing the esters described in (A) above and (C) below are described by the formula (B):

wherein R corresponds to $R_1$ and $R_2$ as defined above in formula (A) and x encompasses all the values of m and n. A variety of alcohols so defined are readily available by the ethoxylation, e.g., of hexanol, heptanol, 2-ethyl hexanol, decanol, propanol, isobutanol, octanol, dodecanol, octadecanol and the like including linear and branched isomers in which R is an alkyl radical containing 3 to 18 carbon atoms.

A number of commercially available alcohols with an even number of carbon atoms in the range of $C_6$ to $C_{20}$, derived from ethylene growth technology and preferably containing ten to fourteen carbon atoms, are desirable for preparing the ethoxylated alcohols described by formula (B). The ethylene oxide adducts corresponding to the formula (B) are well known and can be prepared by the reaction of up to 50 moles of ethylene oxide per mole of alcohol and preferably from about 5 to 20 moles of ethylene oxide per mol of alcohol. Representative ethoxylated alcohols include those which are listed below:

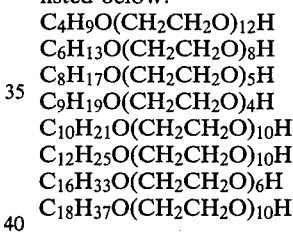

Half esters of α-sulfosuccinic acid suitable for use in the present invention are described by formula (C):

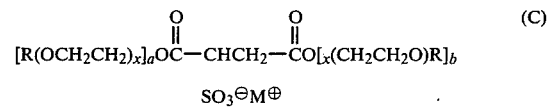

$$SO_3^\ominus M^\oplus$$

wherein R is as defined for formula (B), x encompasses all values of m and n and one of the "a" bracket entity and "b" bracket entity is replaced by cation M as defined above.

The preparation of the compounds described by formulas (A) and (C) are broadly known in the art. The diesters according to formula (A) are potentially available by reacting maleic anhydride with ethoxylated alcohol and sodium bisulfite in a molar ratio of 1:2:1. The half-esters according to formula (C) are prepared by using the same reactants in a molar ratio of 1:1:1.

Suitable parameters for use in the present invention are tabulated below. Since the function of the sulfosuccinate derivative is to greatly diminish or to eliminate the tendency of the petroleum sulfonate to precipitate on contact with hard brines containing high concentration of divalent ions such as $Ca^{++}$ and/or $Mg^{++}$, the weight ratio of the sulfosuccinate to the petroleum sulfonate in the surfactant system is critical.

|  | (Petroleum Sulfonate) | | (Sulfosuccinate) | |
| --- | --- | --- | --- | --- |
|  | Broad Range | Preferred Range | Broad Range | Preferred Range |
| wt.%* | 0.01–15.0 | 2.5–7.0 | 0.01–15.0 | 0.25–3.5 |

*This weight percent is based, respectively, on the weight of active sulfonate and weight of sulfosuccinate compared to the weight of water in the surfactant system comprising brine, sulfosuccinate, petroleum sulfonate and cosurfactant.

The now preferred range for the ratio of the weight percents of the sulfosuccinate and the petroleum sulfonate is 1:10 to 50:1. The ranges for the petroleum sulfonate, cosurfactant and salt concentration in the initially constituted surfactant system are as follows: the concentration of petroleum sulfonate in the aqueous composition is about 0.01 to 15 weight percent active ingredient based on the weight of water, preferably 2 to 5 weight percent; when used, the concentration of cosurfactant is about 1 to 7, preferably 1.5 to 4 weight percent based on the weight of water (the cosurfactant to surfactant ratio should be in the range of about 0.25:1 to 1.5:1, preferably about 0.5:1 to 1:1) and the concentration of salt is within the range of 250 to 100,000, more preferably 500 to 40,000, most preferably 5,000 to 25,000, parts per million total dissolved solids.

The following tabulation describes the inventive compositions in terms of broad and preferred ranges for the various components.

| Surfactant System Components | Broad Range wt.%$^a$ | Preferred Range wt.%$^a$ |
| --- | --- | --- |
| Surfactant (e.g., petroleum sulfonates) | 0.01–15 | 2.5–7 |
| Cosurfactant (e.g., isobutyl alcohol) | 1–7 | 2–5 |
| Protective Agent [e.g., see generic formula (A)] | 0.01–15 | 0.25–3.5 |
| Electrolyte (ppm) | 250–100000 | 5000–25000 |
| Cosurfactant/Surfactant (% wt. ratio) | 0.25:1–1.5:1 | 0.5:1–1:1 |
| Protective Agent/Surfactant (% wt. ratio) | 1:10–50:1 | 1:1–5:1 |
| Water | 100 | 100 |

$^a$Wt. % is based on weight of water.

The inventive systems displayed phase stability on the addition of up to 32,000 ppm $Ca^{++}$ (see experimental section).

Cosurfactants suitable for use in the present invention include the $C_3$ to $C_6$ aliphatic alcohols such as isopropanol, isobutyl alcohol, pentanol, hexanol, and the like; ketones such as acetone, methylethyl ketone and the like; aldehydes such as acetaldehyde, isobutyraldehyde and the like; esters such as methyl acetate, ethyl acetate, and the like; phenolic compounds such as phenol and the cresols; and amines such as pentylamine and hexylamine. The now preferred cosurfactant for use in the present compositions is isobutyl alcohol.

Supporting experimental data for the present invention were obtained by the following procedures each of which is described below:
 (a) Salt Titrations
 (b) Time Stability Tests
 (c) Core Runs
 (d) Phase Behavior Analysis
 (e) Interfacial Tension Measurements (a) Salt Titrations A stock solution of a selected divalent metal cation-containing salt such as $CaCl_2$ or $MgCl_2$ was prepared and titrated into the inventive surfactant system comprising petroleum sulfonate and the sulfosuccinate protective agent. Control runs were carried out which contained petroleum sulfonate but did not contain the protective agent.

The salt titrations were carried out in a specially designed cell illustrated in the drawing.

Figure 1:
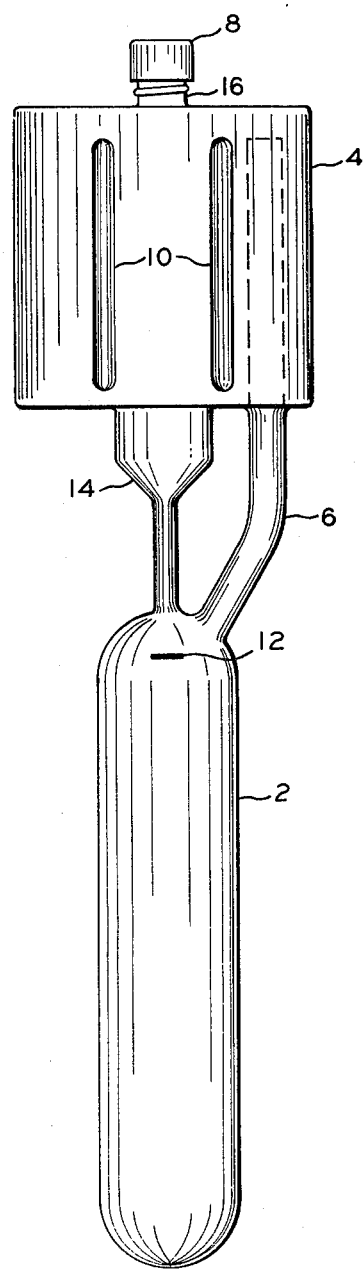
FIG. 1 is an elevational view of the phase stability cell.
Figure 2:
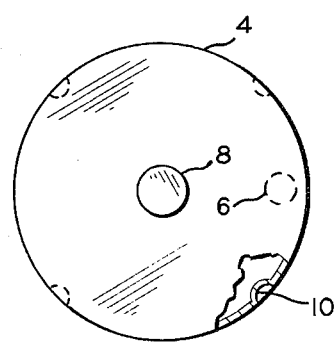
FIG. 2 is a plan view of the phase stability cell partially in cross-section.

Referring now to FIGS. 1 and 2, the cell consists of an upper flat-bottomed cylindrical compartment 4 and a lower round-bottomed cylindrical compartment 2; the bottom of said upper compartment 4 being interconnected with the top of said lower compartment 2 by an offset angular pressure equalizing tube 6 and a centrally located truncated passageway 14. Said upper compartment 4 in its top surface bears a centrally located threaded tubular opening 16 which can be sealed with a plastic cap 8.

Referring to FIG. 1, the upper flat-bottomed cylindrical compartment 4 bears four equally spaced indented stirring baffles 10 in its wall and is penetrated through its floor to approximately its full length by the offset pressure equalizing tube 6. The lower round-bottomed cylindrical compartment 2 bears a calibration mark (indicia) 12 corresponding to a lower compartment volume of 40 ml. The entire apparatus is fabricated of Pyrex glassware.

In operation, the phase stability cell is used to measure viscosity changes and determine light transmittance values for aqueous surfactant systems which are undergoing treatment with aliquots of hard brine. In general, phase stability in such systems is manifested by no or relatively small changes in viscosity and light transmittance as well as no precipitation and/or phase separation on hard brine addition. The cell is calibrated for viscosity measurements by introducing approximately 50 ml portions of individual liquids with known viscosities into compartment 2 via opening 16 and truncated passageway 14. Said 50 ml sample partially fills the upper larger diameter portion of said truncated passage 14. With the cell sealed with plastic cap 8, said cell is inverted so that the liquid of known viscosity is transferred from lower compartment 2 into the upper compartment 4 via the offset angular pressure equalizing tube 6. On returning said cell to an upright position, the liquid sample flows to lower compartment 2 through truncated passageway 14 and the time required for the liquid level in lower compartment 2 to rise to the 40 ml calibration mark (indicia) 12 is determined by a stopwatch. The procedure is repeated for any convenient number of liquids with a range of known viscosities and a plot of times and viscosities yields a calibration curve which can be used for establishing the viscosities of other liquids. Experimentally, the liquid of interest is placed in the cell as hereinabove described and the time interval required for passage of 40 ml of liquid through the truncated passage 14 is determined.

Light transmittance values of liquid samples contained in the lower compartment 2 are obtained by placing the round-bottomed cylindrical compartment 2 in the sample holder of a colorimeter and reading the transmittance.

Hard brine is added to the apparatus at 16.

The viscosity and light transmittance measurements are individually determined after each successive addition of hard brine and the procedure is continued until precipitation and/or phase separation is observed or until a maximum total volume of 50 ml of the hard brine has been added. After the addition of each hard brine aliquot the cell is sealed with plastic cap 8 and the apparatus manually shaken to effect good mixing or the cell and its contents is horizontally positioned for roller mixing. If the latter technique is used, the upper compartment 4 contacts the rollers and the lower compartment 2 is supported by insertion into an anchored teflon sleeve, said sleeve fitted loosely enough to allow free rotation of compartment 2 in said sleeve cavity during the mixing process.

During each titration, the optical properties of the test sample were followed by the use of a colorimeter equipped with a red filter and red sensitive phototube. At a wavelength of 750 millimicrons, the transmittance reading on the colorimeter was initially set at 1.0 with the sample cell containing the surfactant system.

The untitrated sample was examined prior to the titration in regard to birefringence and viscosity. The latter property was determined by measuring the time required for 40 ml of the solution to pass from the upper compartment of the cell to the lower compartment. The viscosity corresponding to this time period was read off a calibrated chart based on times of samples with known viscosities.

The birefringence or lack thereof in the initial test sample (50 g) was determined by positioning the filled sample tube between two crossed polarized lenses mounted before a 100 watt illuminating lamp and rocking it gently. Birefringence or streaming birefringence in these samples resulted in the appearance of interferometer lines (a pattern of alternating bright and dark areas characteristic of dispersed light).

In carrying out the titrations, an appropriate volume of titrant was added to the cell. The cell was sealed and agitated for about 50 seconds before successively determining viscosity, transmittance and birefringence as previously described. The system was visually examined for phase separation and/or precipitation before the above steps, starting with the addition of an appropriate volume of titrant, were repeated. The procedure for each sample was terminated after the addition of 50 ml of titrant or at the appearance of a precipitate and/or phase separation.

Figure 3:
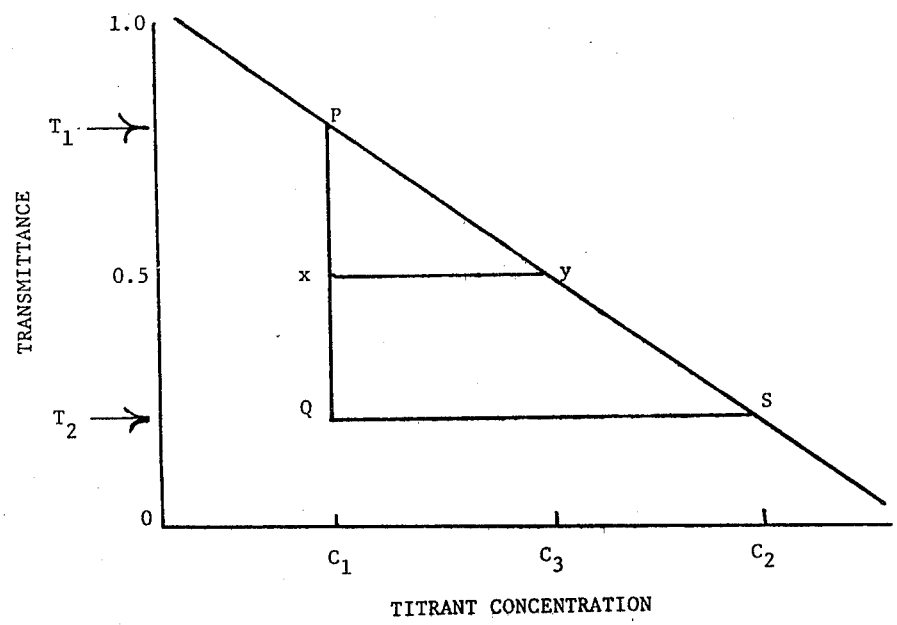
FIG. 3 is a "half-point" calculation diagram.

In the data presented hereinbelow, the so-called "half-point" of a sample refers to the titrant concentration at which the transmittance of the test mixture was one-half, i.e., 0.5, of the initial value of 1.0. The "half-point" can be calculated by linear interpolation based on transmittance values on either side of $T = 0.5$, e.g., if $C_1$ is the titrant concentration with a transmittance reading of $T_1$, which is greater than 0.5, and $C_2$ is the titrant concentration with a transmittance reading of $T_2$ which is less than 0.5, then the "half-point" concentration $C_3$ corresponding to a transmittance of 0.5 can be calculated by considering the relationships derived from similar triangles PQS and PXY of the diagram of FIG. 3.

By definition, triangles PXY and PQS are similar and by the law of similar triangles it follows that $$\frac{\overline{PX}}{\overline{PQ}} = \frac{\overline{XY}}{\overline{QS}}$$

and expressing $\overline{PX}$, $\overline{PQ}$, $\overline{XY}$, and $\overline{QS}$ in terms to $T_1$, $T_2$, $C_1$, $C_2$ and $C_3$ from the diagram and substituting in the above expression gives $$\frac{(T_1 - 0.5)}{(T_1 - T_2)} = \frac{(C_3 - C_1)}{(C_2 - C_1)}$$

which on simplifying gives $$(C_2 - C_1)\left(\frac{T_1 - 0.5}{T_1 - T_2}\right) + C_1 = C_3 \text{ ("half-point" value)} \quad (1)$$

Thus, any half-point concentration value, $C_3$, can be calculated by use of the above general expression using $C_1$, $C_2$, $T_1$ and $T_2$ based on experimental work.

Figure 4:
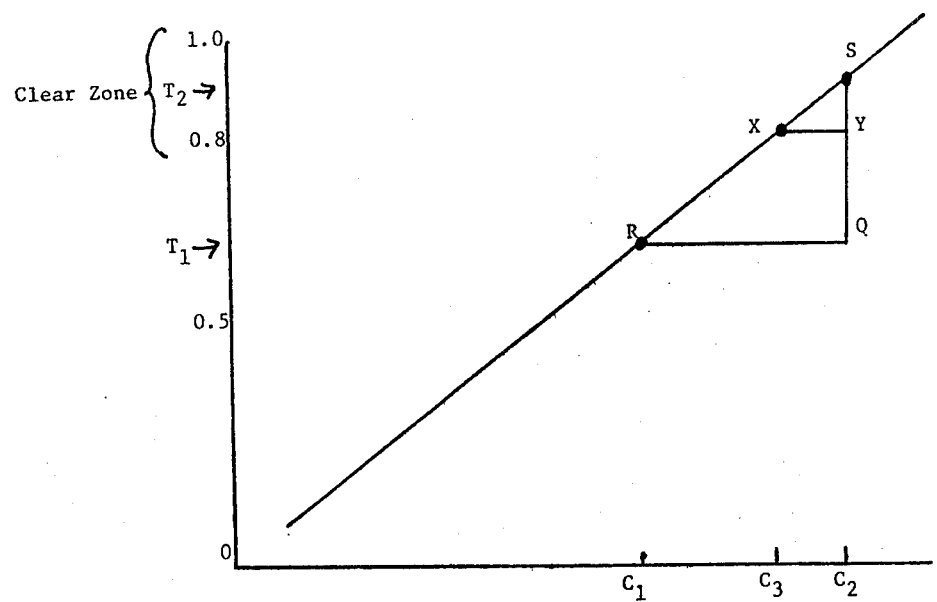
FIG. 4 is a "clear zone" approximation diagram.

The so-called "clear zone" of a sample originates at a concentration corresponding to a transmittance value of 0.8. The concentration corresponding to a transmittance of 0.8 can be calculated by linear interpolation based on transmittance values on either side of $T=0.8$, e.g., if $C_2$ is the titrant concentration with a transmittance reading of $T_2$, which is greater than 0.8, and $C_1$ is the titrant concentration with a transmittance reading of $T_1$ which is less than 0.8, then the corresponding $C_3$ corresponding to a transmittance of 0.8 can be calculated by considering the relationships derived from similar triangles RSQ and XYS of the diagram of FIG. 4, wherein:

$$\frac{\overline{SY}}{\overline{SQ}} = \frac{\overline{XY}}{\overline{RQ}}$$

and expressing $\overline{SQ}$, $\overline{SY}$, $\overline{RQ}$ and $\overline{XY}$ in terms of $T_1$, $T_2$, $C_1$, $C_2$ and $C_3$ from the diagram and substituting in the above expression gives $$\frac{(T_2 - 0.8)}{(T_2 - T_1)} = \frac{(C_2 - C_3)}{(C_2 - C_1)}$$

which on simplifying gives $$(C_2 - C_1)\left(\frac{T_2 - 0.8}{T_2 - T_1}\right) = C_2 - C_3$$

$$C_3 = C_2 - \left(\frac{T_2 - 0.8}{T_2 - T_1}\right)(C_2 - C_1)$$

The above equation is of the same general form as the expression used hereinabove for the calculation of the half-point of a sample.

Figure 5:
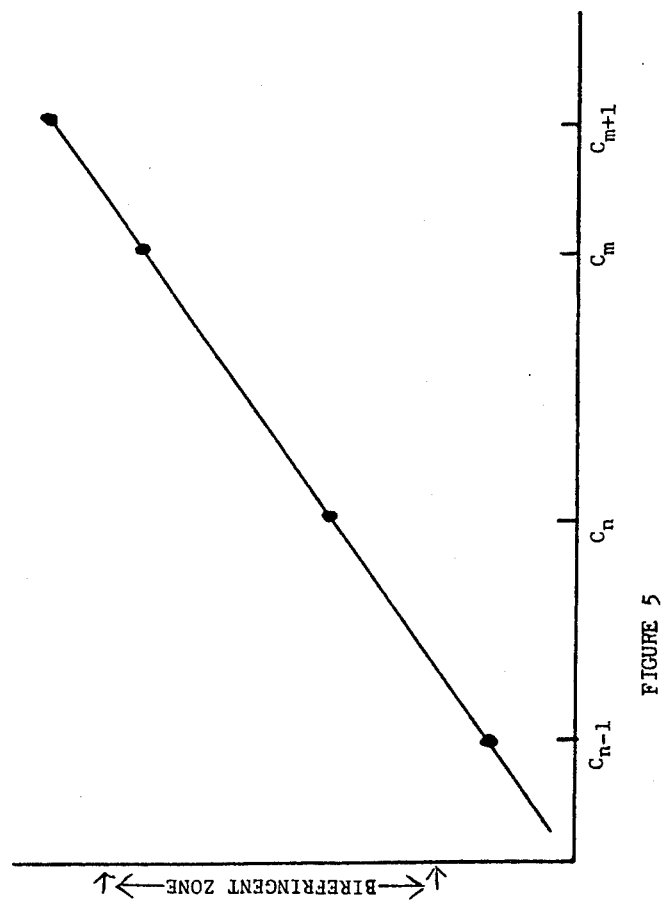
FIG. 5 is a "birefringence zone" approximation diagram.

A birefringence zone is bound by two limiting titrant concentrations within which the system was observed to be birefringent. The diagram of FIG. 5 can be used to illustrate the approximation of these limits.

In this diagram, $C_n$ and $C_m$ are, respectively, the lowest and highest experimentally determined concentrations at which the system exhibited birefringence. The experimentally determined concentrations $C_{n-1}$ and $C_{m+1}$ are, respectively, the lowest and highest experimentally determined concentrations at which the system did not exhibit birefringence. By averaging, the lower and upper limits of the birefringence zone, respectively, $L_1$ and $L_2$, are estimated by the following espressions:

$$L_1 = C_{n-1} + \frac{C_n - C_{n-1}}{2} \quad (2)$$

$$L_2 = C_{m+1} - \frac{C_{m+1} - C_m}{2} \quad (3)$$

The limits of phase separation, precipitation and viscosification can be estimated in a similar fashion.

A viscosification zone can develop in the test mixture during the titration as evidenced by the time necessary for 40 ml of fluid to pass through the constriction of the titration cell. By determining the volume of titrant added to the sample when its viscosity first exceeded or dropped below 50 cp, the concentration of titrant in the sample at those points can be calculated from equations 2 and 3. These concentrations of titrant are listed as the limits of the viscosification zone.

Phase separation and precipitation points can also be expressed in terms of titrant concentrations calculated from equation 2.

From the salt titration results, in general, the most promising candidates for use as surfactant systems in hard brines exhibit high half-points, wide birefringence zones, no viscosification zones, high phase separation points and high precipitation points. Titrants containing 9 or more weight percent monovalent cations and 6 or more weight percent divalent cations are recommended in the salt titration tests to minimize dilution errors.

(b) Time Stability Tests

Time stability tests were carried out by placing approximately 50 g mixtures of protective agent and surfactant system in a closed vial and then determining transmittance, birefringence, and phase stability over an extended time period. During this time period no additional components were added to the mixtures which were allowed to age at ambient temperature. Phase separation and/or precipitation during the time stability test eliminated certain samples in preliminary screening. Systems which exhibited streaming birefringence were considered promising candidates for oil recovery.

(c) Core Run (see Example IV)

A core run was carried out in Berea sandstone at about 96° F. As is well known in the art, the core was brought to a state of waterflood residual oil by the following steps: (1) the core was evacuated by vacuum pump to a low pressure and saturated with brine, (2) flooded with oil to an irreducible water saturation, and (3) flooded with water to an irreducible oil saturation. At this point, the core system simulates a reservoir which has been water flooded.

Oil recovery from the core was effected by the sequential injection of the following materials: (1) an optional brine preflush slug to further adjust the salinity of the system to a specified level, (2) a surfactant system slug comprising an inventive composition as hereinabove described, (3) a thickened aqueous slug (mobility buffer) to propagate fluids through the core and (4) optional aqueous drive slug such as brine to complete the transfer of displaced oil and water to a collection vessel.

(d) Phase Behavior Analysis (see Example III)

The phase behavior was determined by the equilibration method which involves the mixing of individual samples of a specified oil with a series of given surfactant systems prepared in brines of different salinities. The equilibrations are carried out in glass-stoppered graduated cylinders which are shaken and incubated at a specified temperature until phase volumes remain constant with time. As hereinbelow described in greater detail, the various equilibrated systems exhibit, respectively, two, three and two phases corresponding to the increasing salinity levels in the surfactant systems. Thus, equilibration of a hydrocarbon such as a crude oil with aqueous surfactant systems containing progressively higher salt concentrations can typically give rise to the following types of phase behavior:

(a) Region I: Two Phases (Relatively Low Salinity):

The equilibration of the surfactant system and oil results in an upper phase consisting essentially of oil and a water-rich lower phase microemulsion comprising water, surfactant, oil and cosurfactant (gamma-type microemulsion).

(b) Region II: Three Phases (Intermediate Salinity):

The equilibration of the surfactant system and oil results in an upper phase consisting essentially of oil, a middle phase microemulsion comprising water, oil, surfactant and cosurfactant and a bottom phase comprising water (beta-type microemulsion).

(c) Region III: Two Phases (Relatively High Salinity):

The equilbration of the surfactant system and oil results in an oil-rich upper phase microemulsion comprising water, oil, surfactant and cosurfactant and a lower phase comprising water (alpha-type microemulsion).

Oil recoveries in the so-called intermediate salinity range are generally good and optimal at that salinity whereat the interfacial tension values approach a minimal value. Example III, disclosed hereinbelow, demonstrates that the instant surfactant system comprising brine-surfactant-cosurfactant-oil-sulfosuccinate protective agent exhibits phase behavior similar to selected brine-surfactant-cosurfactant-oil systems.

(e) Interfacial Tension Measurements

These measurements were carried out by standard methods.

The following working examples illustrate the operability of the instant invention.

EXAMPLE I

Salt titration results tabulated in Table I demonstrate that the alkylethoxysulfosuccinates functioned as protective agents for petroleum sulfonates in hard brines. These protective agents greatly diminished the tendency of the surfactant to phase-separate or precipitate on contacting significant concentrations of $Mg^{++}$ and $Ca^{++}$.

In Table I inventive run 2 demonstrates that the protective agent sulfosuccinate rendered the sample phase stable at calcium ion concentrations above 5000 ppm (phase separation was observed at 5846 ppm $Ca^{++}$) whereas the control sample exhibited precipitation at about 784 ppm $Ca^{++}$. Thus, the inventive system can tolerate up to seven times the concentration of calcium cation. A similar examination of the magnesium titrations shows the inventive system (runs 5 and 6) to be of the order of 25 times more tolerant of magnesium than the control run 4.

The existence of the birefringence zones in the inventive runs 2, 3, 5 and 6 suggests that these systems would be effective in post-primary oil recovery.

EXAMPLE II

The results tabulated in Table II indicate the improved time stability of the inventive systems over the control runs.

TABLE I

Salt Titration Data on Surfactant Systems in Hard Brines

| Run No. | Run Type[a] | Titrant Cation | Half-Point[b] | Birefringence Zones[b] | Phase Separation[b] | Precipitation Point[b] |
|---|---|---|---|---|---|---|
| 1 | Control | $Ca^{++}$ | 319 | $NO^c$ | $NO^c$ | 784.4 |
| 2 | Invention | $Ca^{++d}$ | 677 | 1544–5846 | 5846 | $NO^c$ |
| 3 | Invention | $Ca^{++d,e}$ | $NO^c$ | 1134–5621 | 5621 | $NO^c$ |
| 4 | Control | $Mg^{++}$ | 229.8 | $NO^c$ | $NO^c$ | 784.0 |
| 5 | Invention | $Mg^{++d}$ | 1711 | 6154–21381 | 21381 | $NO^c$ |
| 6 | Invention | $Mg^{++d,e}$ | $NO^c$ | 3083–21080 | 21080 | $NO^c$ |

[a]Control samples contained 3 weight percent active Witco petroleum sulfonate TRS-10-395 in distilled water.
[b]These results are given in terms of ppm reflecting the amounts of titrant cation present in the sample.
[c]NO represents "not observed."
[d]These runs contained 2 weight percent of the sulfosuccinate protective agent.
[e]These runs contained 3 weight percent ethanol as well as 2 weight percent of the sulfosuccinate protective agent.

TABLE II

Time Stability Tests at Ambient Temperature for 30 Days

| Run No. | Run Type | Added Cation (ppm) | Phase Stability |
|---|---|---|---|
| 7 | Control[a] | $Ca++$ (250) | yes |
| 8 | Control[a] | $Ca++$ (500) | no |
| 9 | Invention[b] | $Ca++$ (3000) | yes |
| 10 | Invention[b] | $Ca++$ (4000) | no |
| 11 | Control[a] | $Mg++$ (0.0) | yes |
| 12 | Control[a] | $Mg++$ (250) | no |
| 13 | Invention[b] | $Mg++$ (20000) | yes |
| 14 | Invention[b] | $Mg++$ (25000) | no |

(a) Control samples contained 3 weight percent active Witco petroleum sulfonate TRS-10-395.
(b) These runs contained 2 weight percent of the sulfosuccinate protective agent.

The inventive runs of Table II, i.e., 9, 10, 13, and 14 show, respectively, that the sulfosuccinate stabilizes the system to between 3000 and 4000 ppm calcium and to between 20000 and 25000 ppm magnesium.

EXAMPLE III

The results shown in Table III indicate that the equilibration of oil with the inventive surfactant system gave a three phase region at intermediate salinity and within that salinity range the sulfosuccinate-containing system exhibited lower interfacial tension values than a control system containing a sulfated ethoxylated alkylphenol.

The results in Table III (see the invention runs) verify that the interfacial tension values for the inventive sulfosuccinate systems were lower than observed for the closely related control system containing the sulfated ethoxylated alkylphenol.

EXAMPLE IV

Core Test

TABLE III

Equilibrated Phase Behavior in Brine-Surfactant-Cosurfactant-Sulfosuccinate Systems

| Petroleum Sulfonate Identification Number | Type of Run | Protective Agent | Alcohol Cosurfactant | Interfacial Tension* | Approximate[c] Salinity NaCl (ppm) |
|---|---|---|---|---|---|
| 46 | Control | Alipal EP-110[a] | Isobutyl | 0.0035 | 31,000 |
| 46 | Invention | Alkasurf[b] | Isobutyl | 0.0025 | 29,000 |
| 44 | Control | Alipal EP-110 | Isobutyl | 0.00059 | 22,000 |
| 44 | Invention | Alkasurf | Isobutyl | 0.00040 | 19,500 |
| 44 | Control | Alipal EP-110 | tert-Butyl | 0.0012 | 35,000 |
| 44 | Invention | Alkasurf | tert-Butyl | 0.00094 | 27,000 |
| 46 | Control | Alipal EP-110 | tert-Butyl | 0.0034 | 58,000 |
| 46 | Invention | Alkasurf | tert-Butyl | 0.0034 | 52,000 |

*Intersection of interfacial tension values for water-microemulsion interface and oil-microemulsion interface within three-phase β-region.
[a]Alipal (a trademark) EP-110 is a commercially available sulfated ethoxylated alkylphenol [p—$C_9H_{19}C_6H_4(OC_2H_4)_9SO_4NH_4$].
[b]Alkasurf (a trademark) is a commercially available sulfosuccinate ester of an ethoxylated alcohol [$C_{10}H_{21}(OC_2H_4)_6O_2CCH_2CH(SO_3Na)CO_2(C_2H_4O)_6C_{10}H_{21}$].
[c]Salinity corresponding to the intersection of interfacial tension curbes.

A core test was run using the inventive system as the recovery agent. The test was conducted in a cylinder of Berea sandstone, 3 feet long and 3 inches in diameter. Berea sandstone is a commercially available sandstone mined and machined by Cleveland Quarries Company, Amherst, Ohio 44001. The core was prepared for flooding by sheathing the rock in a 1 inch thick coating of epoxy mixed 3 to 1 by weight with diatomaceous earth. This sheath produced an impenetrable cover on the core.

The core was then connected to a vacuum pump and was evacuated until a constant pressure of one micron of mercury was achieved. The evacuated core was disconnected from the pumps and was connected to a dispensing vessel filled with South Cowden connate brine. The core filled with 898 ml of this brine, thus establishing the pore volume of the core as 898 ml. The composition of South Cowden connate brine is given in Table A. For the remainder of the test, the core was maintained at a temperature of 96° F.

The core was flooded with South Cowden crude oil by injecting the oil into one end of the horizontal cylinder and collecting the fluid produced from the other end of the core. Injection continued until no more brine was produced from the core. At this point, 25 pore volumes of oil had been injected into the core and 646 ml of South Cowden connate brine had been recovered from the core. The space previously occupied by the brine was now occupied by the oil so the core contained 646 ml of South Cowden oil, representing an initial oil saturation of 71.9 volume percent. Data for South Cowden crude oil are given in Table B.

A waterflood was conducted in the same manner as the oilflood described above. The injection of 27 pore volumes of South Cowden connate brine recovered 350 ml of oil, thus leaving the core with a waterflood residual oil saturation of 32.96 volume percent (296 ml/898 ml). Upon completing the waterflood, the core was ready for treatment with the inventive recovery system.

Three fluids were injected into the core while testing the inventive system. These fluids were a preflush of brine, a surfactant solution, and a polymer solution. The preflush of one half pore volume of brine, 450 ml, served to minimize contact between the South Cowden connate brine and the surfactant solution. The brine used in the preflush was Hendricks Reef water containing 10,000 ppm sodium chloride. The composition of Hendricks Reef is given in Table C. The preflush was followed with 89.8 ml of surfactant solution, one tenth of a pore volume. The composition of the inventive surfactant system is given in Table D. The last fluid injected was the polymer solution, commonly known as a mobility buffer. The composition of the polymer solution is given in Table E. The volume of polymer solution injected was 891 ml.

The effluent from the core was collected and measured. A total of 117 ml of oil was recovered, representing 39.53 volume percent of the 296 ml of waterflood residual oil contained in the core when the test of the inventive system started. Data on the effluent samples are contained in Table F.

This test showed that the surfactant compositions described in this case will recover a significant fraction of the oil left in a reservoir by a waterflood.

TABLE A

Composition of South Cowden Connate Water

| Ion | Concentration (ppm) |
|---|---|
| Calcium | 3,321 |
| Magnesium | 831 |
| Chloride | 46,525 |
| Sulfate | 3,647 |
| Bicarbonate | 869 |
| Sodium | 26,746 |
| Total Divalent Cations | 4,152 |
| pH of brine = 7.0 | |

TABLE B

Data for South Cowden Crude Oil

| | |
|---|---|
| Oil Viscosity | 7.7 centipoise |
| Oil Equivalent Alkane Carbon Number | 10.8 |
| Oil Density | 0.8580 g/cm$^3$ |
| Oil Nitrogen Content | 1,142 ppm |
| Oil Sulfur Content | 1.9 weight % |

TABLE C

Hendricks Reef Water Composition

| Component | Concentration (ppm) |
|---|---|
| Calcium | 947.6 |
| Magnesium | 299 |
| Chloride | 4,378 |

TABLE C-continued

Hendricks Reef Water Composition

| Component | Concentration (ppm) |
|---|---|
| Sulfate | 2,498 |
| Bicarbonate | 393 |
| Sodium | 2,531 |
| Divalent Cations | 1,247 |
| Total Dissolved Solids | 11,045 |
| pH of brine = 7.6 | |

TABLE D

Composition of Surfactant Solution

| Component | Concentration (weight percent) |
|---|---|
| Petroleum Sulfonate[1] | 5.0 |
| Alkasurf SS-DA-6 | 1.0 |
| Sodium Chloride | 1.0 |
| 2-methyl-1-propanol (isobutanol) | 3.0 |
| Hendricks Reef Water | 90.0 |

[1]An ammonium petroleum sulfonate was made from Kansas City atmospheric gas oil. The sulfonate has an equivalent weight of 375 units and an analysis of:
77.1 weight percent sulfonate
14.0 weight percent unreacted oil
2.3 weight percent ammonium sulfate
5.3 weight percent water
2.3 weight percent 2-propanol

TABLE E

Composition of Mobility Buffer

| Component | Concentration (weight percent) |
|---|---|
| CMHEC 420-H Polymer[1] | 0.3 |
| Hendricks Reef Water | 99.7 |

[1]CMHEC 420-H polymer is carboxymethylhydroxyethylcellulose

TABLE F

Data for Core Effluent Samples

| Sample No. | Volumes Produced (ml) | | | Injection Pressure | Collection Time (in minutes from start of test) |
|---|---|---|---|---|---|
| | Total | Oil | Water | | |
| 1 | 90 | 0 | 90 | 2 | 553.3 |
| 2 | 79 | 0 | 79 | 1.6 | 1131 |
| 3 | 69 | 0 | 69 | 1.95 | 1645 |
| 4 | 45 | 0 | 45 | 2.4 | 1984 |
| 5 | 94 | 0.5 | 93.5 | 4.5 | 2670 |
| 6 | 120 | 40 | 80 | 5.5 | 3315 |
| 7 | 128 | 32 | 96 | 6.5 | 4002 |
| 8 | 95 | 25.5 | 69.5 | 7.4 | 4516 |
| 9 | 51 | 15 | 36 | 8.0 | 4700 |
| 10 | 260 | 4 | 256 | 9.6 | 6194 |
| 11 | 400 | trace | 400 | 1.8 | 8339 |
| Total | 1,431 | 117 | 1,314 | | |

Also according to the present invention, there is provided a viscosity measuring and, as desired, a light transmittance measuring apparatus as described in connection with the drawing.

Reasonable variation and modification are possible within the scope of the foregoing disclosure, drawing and the appended claims to the invention the essence of which is that an ethoxylated sulfosuccinate is used as an additive to impart phase stability to aqueous saline solutions of petroleum sulfonates containing a surfactant and/or a cosurfactant.

I claim:

1. An apparatus suitable for measuring viscosity comprising a top container and a bottom container, a restricted flow conduit in open communication with the bottom portion of the top container and the top portion of the bottom container, a pressure equalizing conduit in open communication with a locus within the top portion of the bottom container and with a locus within the top portion of the top container, said equalizing conduit entering into said top portion of the top container through the bottom of said top container, a filling means in the top portion of said top container, said apparatus being adapted to receive into the bottom container a measured quantity of liquid, the viscosity of which is to be measured and to pass said measured quantity of liquid at least through said equalizing tube into said top container from said bottom container upon inverting said apparatus so that the time taken for a measured quantity of said liquid to flow from said top container to said bottom container through said restricted flow conduit upon returning said apparatus to its upright position can be measured, said upper container having a diameter greater than said bottom container and said equalizing tube being entirely comprised within the outermost periphery of said top container.

2. An apparatus according to claim 1 wherein viewed along its axis, the apparatus presents a substantially circular cross-section at right angle to said axis.

3. An apparatus according to claim 1 wherein said upper container comprises integrally formed within at least one wall thereof, extending inwardly from said wall, at least one protrusion, said protrusion being adapted to agitate liquid in said top container when it is moved as by shaking or rolling.

* * * * *